United States Patent [19]

Marshall

[11] Patent Number: 5,174,306
[45] Date of Patent: Dec. 29, 1992

[54] METHOD AND APPARATUS FOR FORMING A STERILE FIELD

[75] Inventor: Lyman R. Marshall, Asheville, N.C.

[73] Assignee: Scherer Healthcare Ltd., Asheville, N.C.

[21] Appl. No.: 714,314

[22] Filed: Jun. 10, 1991

Related U.S. Application Data

[63] Continuation-in-part of Ser. No. 518,770, Apr. 30, 1990, abandoned.

[51] Int. Cl.⁵ ............................................. B65B 53/00
[52] U.S. Cl. .................................. 128/849; 128/852; 206/439
[58] Field of Search ............... 206/438, 439, 440, 441; 128/849, 852, 853, 854, 855, 856

[56] References Cited

U.S. PATENT DOCUMENTS

| | | | |
|---|---|---|---|
| 1,436,406 | 11/1922 | Schulz | 206/440 X |
| 3,061,087 | 10/1962 | Scrivens et al. | 206/439 |
| 3,478,868 | 11/1969 | Nerenberg et al. | 206/439 |
| 4,041,203 | 8/1977 | Brock et al. | 206/439 X |
| 4,042,109 | 8/1977 | Barcan | 206/440 |
| 4,124,141 | 11/1978 | Armentrout et al. | 206/439 X |
| 4,270,658 | 6/1981 | Schuster | 206/439 |
| 4,706,839 | 11/1987 | Spence | 206/438 X |
| 4,798,292 | 1/1989 | Hauze | 206/439 |

Primary Examiner—Robert A. Hafer
Assistant Examiner—Sam Rimell
Attorney, Agent, or Firm—Carter and Schnedler

[57] ABSTRACT

There is provided a method and apparatus for forming a sterile surgical field including a sheet which may have at least one hole therein and a container which may be received in the hole so that the hole is completely sealed. A package for shipment and storage is formed by placing the sheet inside of the container, covering the container with a lid or a second container, and sealing the container ensuring the sterility of the inside of the container. When the package is opened, the sheet is removed from the inside thereof and spread out. The inside surface of the container and the sheet form a sterile field.

14 Claims, 5 Drawing Sheets

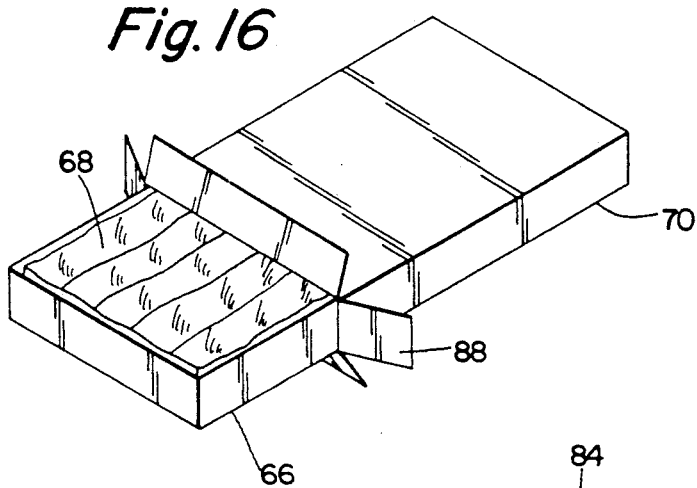
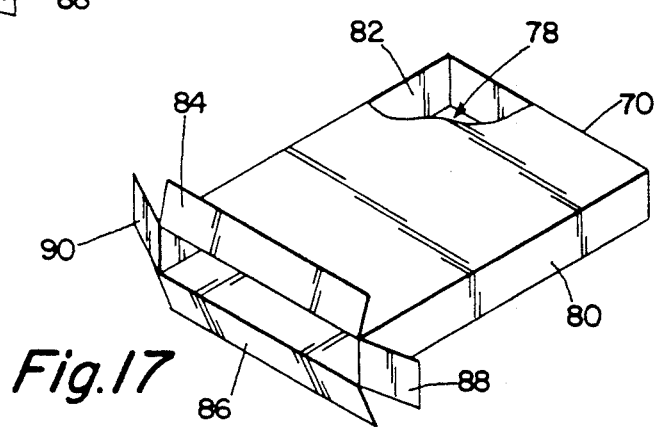
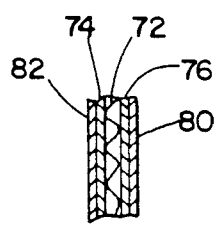
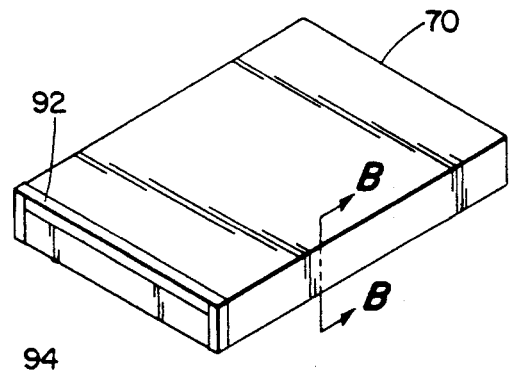
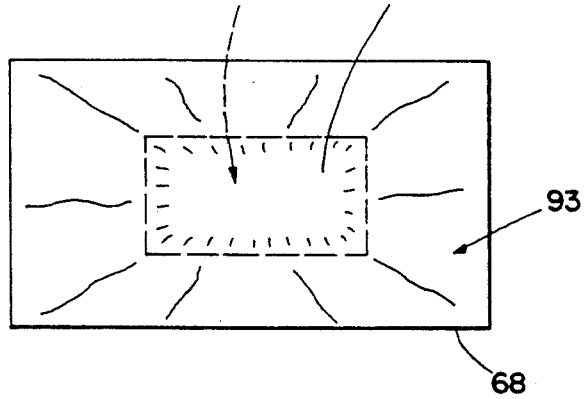

METHOD AND APPARATUS FOR FORMING A STERILE FIELD

This is a continuation-in-part of copending application Ser. No. 518,770 filed on Apr. 30, 1990, now abandoned.

BACKGROUND OF THE INVENTION

This invention relates to apparatus utilized during surgical procedures. More particularly it relates to surgical basins and containers used during surgical procedures which must be used in a sterile field.

Surgical basins are currently used during surgical procedures to receive biological materials and disposable items used during the procedure. The basin is usually made of a hard plastic material. Obviously, the basin must be sterilized before it is taken into the operating room. Normally the basin is sterilized before in a sealed bag to avoid contamination of the basin before use. Because the bag is to provide sterility, it is rather expensive, in some cases costing as much as $1.20. Often a pair of basins are placed in the same bag, one inside the other. A sterile sheet is normally used to wrap the basins prior to placing them in the bag. The sheet is utilized in the operating room to provide a sterile field around the basin. Quite often other surgical devices are placed in one of the basins prior to shipment such as tubing, gloves, gauze, surgical blades, pads, and the like. Thus the basin may carry some rather expensive surgical materials.

It has been found that during shipping and handling of the packaged basins, the outer bag often becomes punctured, thus the entire package is no longer useful since it may no longer be sterile. It is believed that as many as 7 percent of the packaged basins which are shipped become so damaged that disposal is required. Thus the costs are increased proportionally due to this damage. It is therefore desirable to provide a less expensive and better means to provide a sterile package for basins and other surgical materials which also forms a sterile field for use during the surgical procedure.

OBJECTS OF THE INVENTION

It is therefore one object of this invention to provide improved surgical container assembly.

It is another object to provide a surgical container assembly enabling an improved sterile field.

It is a further object to provide a less expensive and more reliable sterile package for use during surgical procedures.

It is still another object to provide a surgical container assembly which is less prone to damage during shipping and handling.

It is yet another object to provide a surgical container assembly which is easier to store and to handle.

It is yet another object to provide a surgical package which is readily sterilizable but impervious to microorganisms and which may be shipped without the need for an additional container.

SUMMARY OF THE INVENTION

In accordance with one form of this invention there is provided a surgical package assembly with at least one container having inner and outer surfaces. A mechanism is provided for closing and opening the container. A sheet is initially received inside of the container. Portions of the sheet are attached to the container. The sheet and the inside surface of the container provides a sterile field when the sheet is removed from the inside of the container and opened out. The container may be covered with a lid or with a second similarly constructed container forming a top. However, in any event the lid or second container must be sealed to the first container to maintain sterility on the inside thereof.

In accordance with another form of this invention, there is provided an apparatus for forming a sterile field including a sheet having a hole therein. A container having an open top is received in the hole with the portions of the sheet around the hole being attached to the container. Thus the hole in the sheet is completely sealed. The inside bottom and side surfaces of the container and the sheet form a sterile field.

In accordance with yet another form of this invention there is provided a method for forming a sterilizable package utilizing a container and a sheet. The method includes forming an opening in the sheet, placing the container in the opening, attaching the sheet to the container in the region around the opening, sealing the opening between the sheet and the container, placing the remainder of the sheet inside the container, and sealing a cover to the open part of the container.

Once the container has been used during a surgical procedure, it may be filled with biological material and used surgical devices. The sheet may be placed back inside the container and the top or the second container placed back on the open top of the first container. The top or second container is then sealed to the first container and the entire package may be conveniently disposed of. Preferably each container includes a lip for attachment to the portion of the sheet around the hole thereof and for receiving sealing tape.

In accordance with still another form of this invention there is provided a method of forming a sterile field utilizing a package including at least one sealed container having a sheet received therein. The container is unsealed and opened. At least a portion of the sheet is placed outside of the container and the sheet is opened or unfolded. The sheet forms a sterile field.

In accordance with yet another form of this invention, there is provided a surgical package including a container for housing surgical materials. The container includes walls which enclose the surgical materials. The walls of the container are lined with a material which permits the passage of sterilizing gas into the inside of the container and thus to the surgical materials but is substantially impervious to microorganisms. A sheet is received inside of the container and when the container is opened, the sheet may be unfolded to present a sterile field.

BRIEF DESCRIPTION OF THE DRAWINGS

The subject matter which is regarded as the invention is set forth in the appended claims. The invention itself, however, together with further objects and advantages thereof may be better understood with reference to the following description taken in conjunction with the accompanying drawings in which:

FIG. 16 is a pictorial view of an apparatus showing still another embodiment of the subject invention showing the inner tray partially removed from the container.

FIG. 17 is a pictorial view of the apparatus of FIG. 16 with the inner tray having been totally removed and with a portion being broken away for clarity.

FIG. 18 is a pictorial view of the apparatus of FIG. 16, however with the inner tray having been sealed inside of the package.

FIG. 19 is a sectional view of a portion of the apparatus of FIG. 18 taken through section line B—B which illustrates the construction of the walls of the container.

FIG. 20 shows the sheet which is received in the tray as shown in FIG. 16 in its open position, and an outline of the tray which remains under the sheet.

DESCRIPTION OF THE PREFERRED EMBODIMENTS

Figure 1:
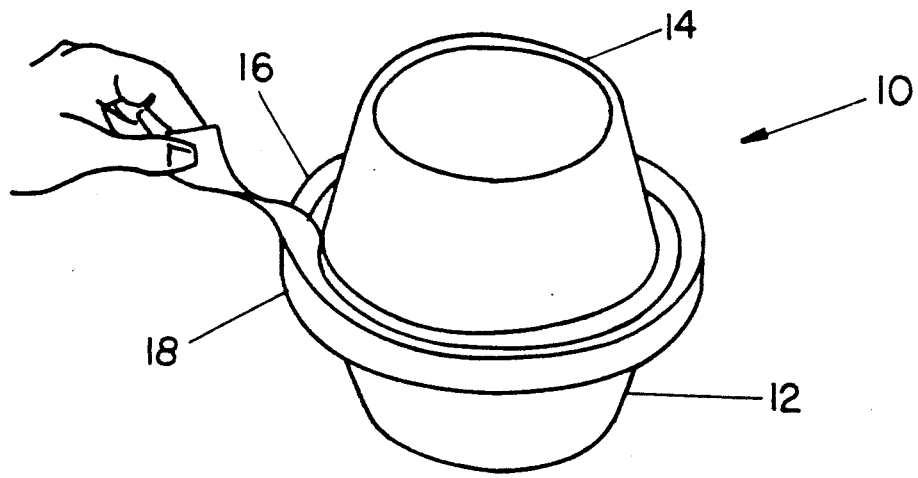
FIG. 1 is a pictorial view of one embodiment of the apparatus of the subject invention.

Referring now more particularly to FIGS. 1-8, there is provided surgical container 10 including lower basin 12 and upper basin 14. In this embodiment upper basin 14 serves as a top for the lower basin. Each basin includes an outer lip 16 which completely circumscribes the basin. The basins are sealed together by a commercially available tape 18 which covers the major portions of the outside surfaces of the outer lips 16 of each basin, thereby ensuring the sterility of the contents on the inside of the basins. The basins are commercially available and commonly referred to as surgical basins and are preferably made of molded polyethylene. The tape 18 may be peeled off by hand and also may be reapplied after the surgical procedure is completed so the container 10 may again be formed to dispose of materials which are placed within the container.

Figure 2:
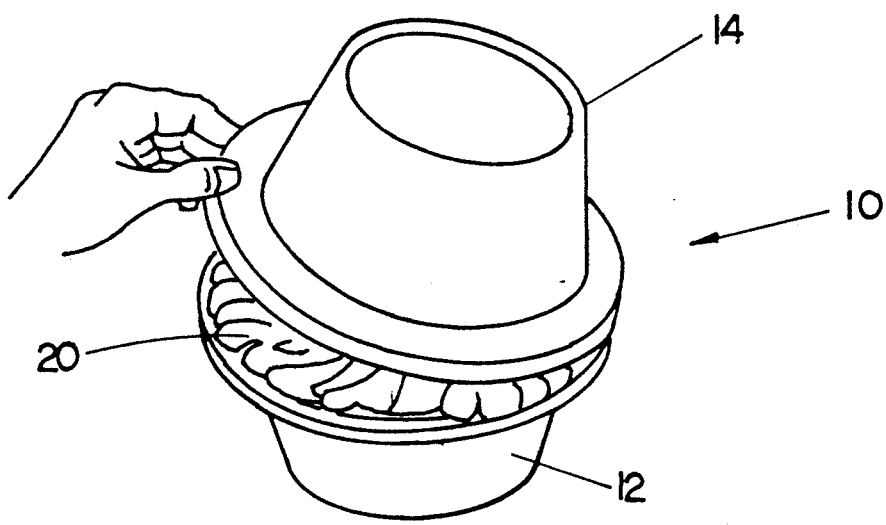
FIG. 2 is a pictorial view of the apparatus of FIG. 2 with the adjacent container being partially separated.
Figure 6:
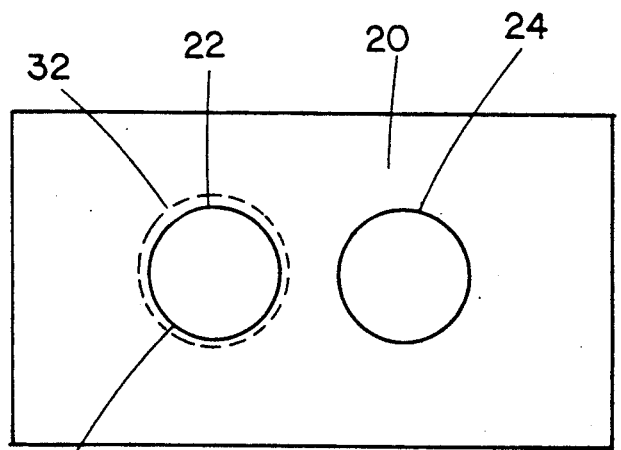
FIG. 6 is a plan view of the sheet of FIG. 5 with the containers removed.

Referring now more particularly to FIG. 2, upper basin 10 is shown being removed from lower basin 12. Sheet 20 is received inside of container 10. As shown in FIG. 6, sheet 20 is formed with two openings 22 and 24. Opening 22 receives basin 12 and opening 24 receives basin 14.

Figure 7:
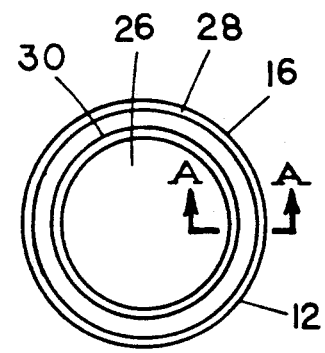
FIG. 7 is a top view of one of the containers of FIG. 1.
Figure 8:
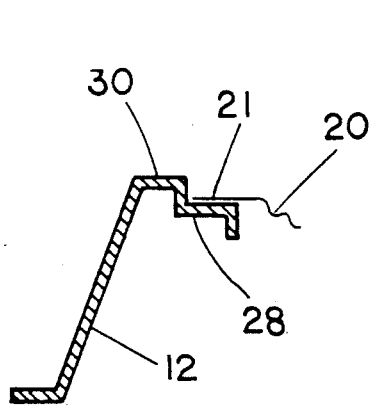
FIG. 8 is a sectional view of a portion of the apparatus shown in FIG. 7 taken through section lines A—A.

As can be seen from FIG. 7, each basin includes lip 16 which circumscribes the inside cup portion 26 of each basin. Lip 16 includes an outer rim 28 and inner rim 30. Inner rim 30 may be slightly raised above the level of outer rim 28. Sheet 20 is adhered to basin 12 by gluing or heat sealing the portion 21 about an inch outside the outer periphery of hole 22, the boundary of which is indicated by dotted line 32, to outer lip 28 as shown in FIG. 8. Contact between basin 12 and basin 14 is provided by inner lips 30 of each basin.

Figure 3:
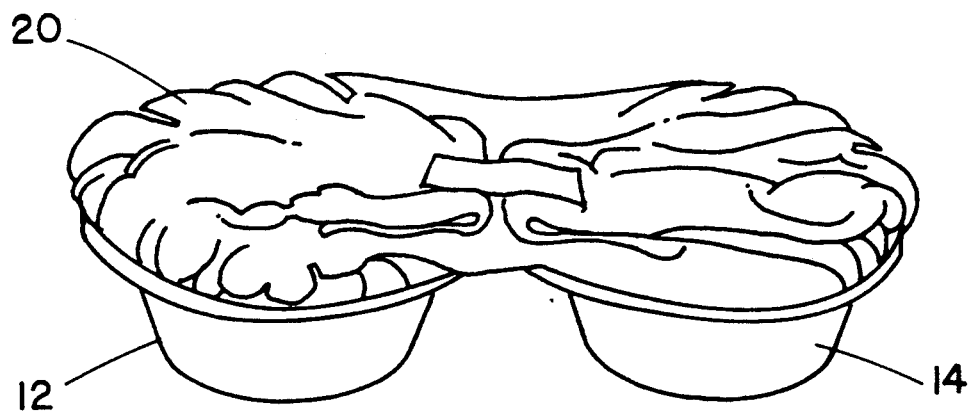
FIG. 3 is a pictorial view of the apparatus of FIG. 1 with the containers being completely separated from one another.

FIG. 8 shows the connection of area 21 of sheet 20 to the outside rim 28 of basin 12. As shown in FIG. 3, sheet 20 is on the inside of basin 12 and the inside of basin 14. Sheet 20 is also attached to basin 14 in the same manner as sheet 20 is attached to basin 12.

Figure 4:
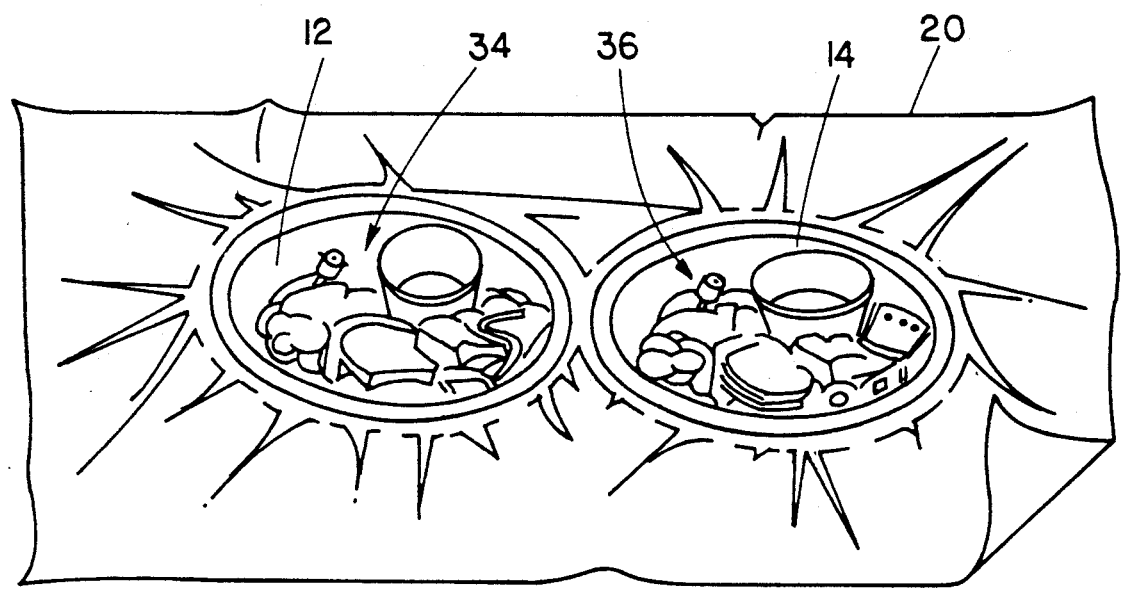
FIG. 4 is a pictorial view of the apparatus of FIG. 3 but with the sheet having been spread open.

Referring now to FIG. 4, sheet 20 is shown fully unfolded thereby exposing surgical articles 34 in basin 12 and surgical articles 36 in basin 14. The surgical articles may include such things as gauze, gloves, tubing, and other apparatus that may be used in a particular surgery. Thus as can be seen from FIG. 4, with the basins fully covering the holes 22 and 24 in sheet 20 and being sealed thereto, with the sheet unfolded, a sterile field is provided for the articles that are within basins 12 and 14.

Figure 5:
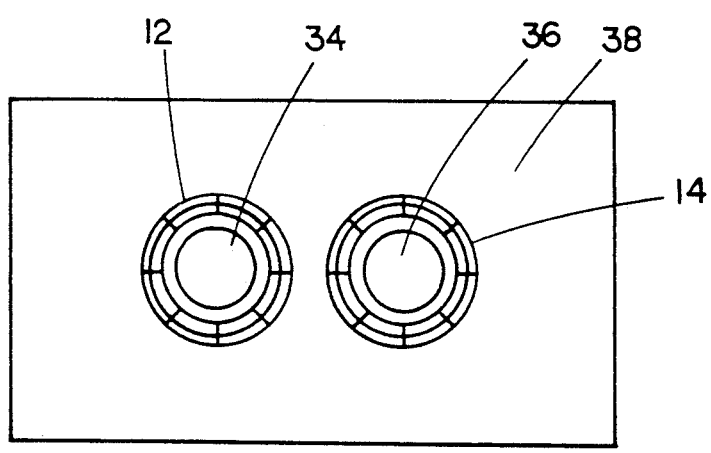
FIG. 5 is a bottom view of the apparatus of FIG. 4.

As can be seen in FIG. 5, the bottom outside surfaces 34 and 36 of basins 12 and 14 respectively and the bottom of sheet 38 form a solid barrier since the sheets are sealed to the outer lips of the basins. A sterile field is thus formed. Bacteria cannot penetrate the apparatus or around the portions where the basins are attached to the sheet.

The apparatus 10 in the condition shown in FIG. 1 provides a sterile package in itself which may be shipped without the need for a sterilizable outer package which may be easily punctured. Because the basins themselves are made of tough polyethylene, it is very difficult to damage them during shipment. Also in the configuration shown in FIG. 1 the package is easy to store, does not readily slide and provides an overall attractive appearance. Furthermore, it is less costly to produce and is easier to use.

Figure 9:
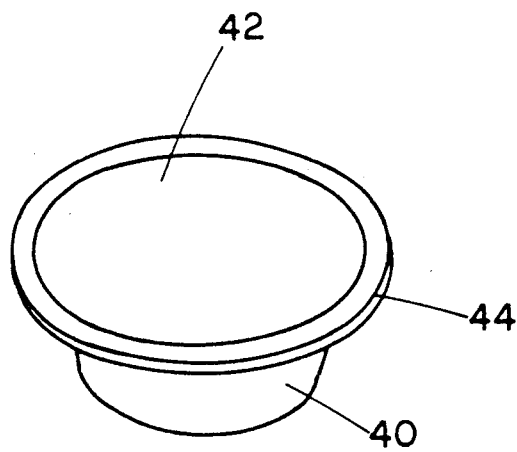
FIG. 9 is a pictorial view of another embodiment of the apparatus of the subject invention.
Figure 10:
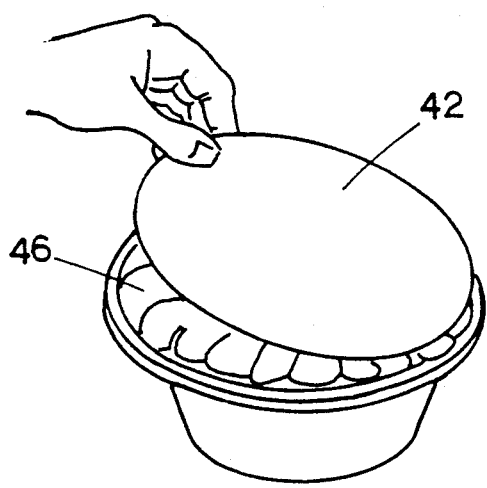
FIG. 10 is a pictorial view of the apparatus of FIG. 9 but with the top being partially removed.
Figure 11:
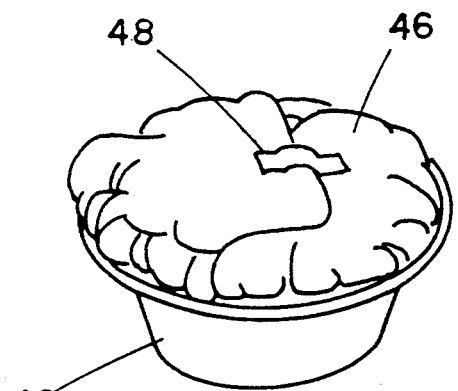
FIG. 11 is a pictorial view of the apparatus of FIG. 9 with the top completely removed.

Referring now more particularly to FIG. 9, there is provided another embodiment of the invention wherein a single basin 40 is utilized having a top 42 which is made of a material impenetrable by bacteria such as medical grade paper, Tyvac, or a light-weight chipboard. Top 42 is attached to basin 40 about its lip by tape 44. As shown in FIG. 10, after removing the tape 44 the top may be removed, exposing sheet 46. Sheet 46 has a single hole therein similar to the double holed sheet shown in FIG. 6 except that the hole is in the center of the sheet. The sheet is attached to a basin 40 in the same manner as basin 12 is attached to sheet 20 as shown in FIG. 8. Tape 48 is used to maintain the sheet in a folded form inside of container 40 as shown in FIG. 11.

Figure 12:
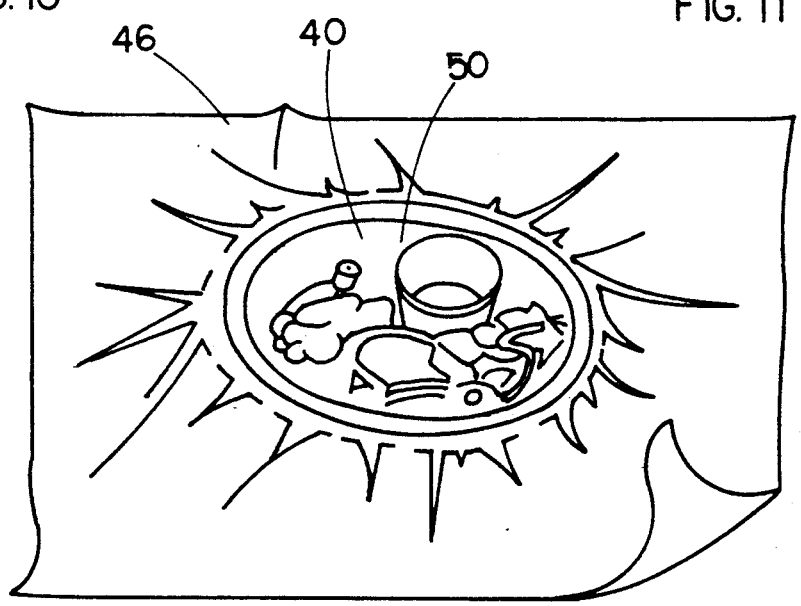
FIG. 12 is a pictorial view of the apparatus of FIG. 8 with the sheet being opened.

As shown in FIG. 12, when the sheet is unfolded, the contents 50 inside of the container 40 are exposed. The combination of container 40 and sheet 46 provides a sterile field for the contents of the container.

The apparatus as shown in FIGS. 9 through 12 are virtually identical to those shown in FIGS. 1 through 8 except that the sheet has a single hole and lid 42 is used instead of second basin 14 to act as a top for basin 40.

Figure 13:
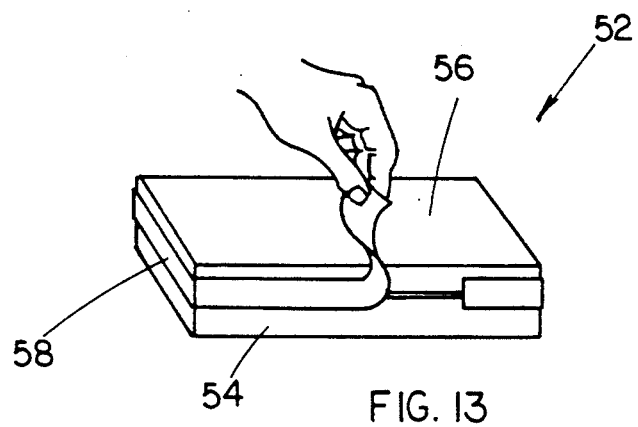
FIG. 13 is a pictorial view of yet another embodiment of the apparatus of the subject invention.
Figure 14:
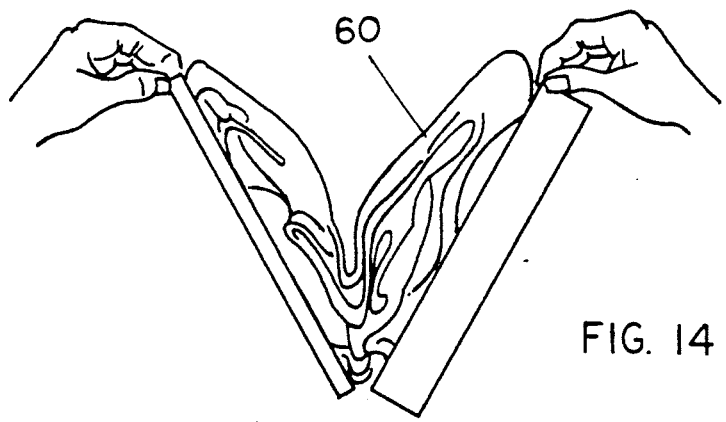
FIG. 14 is a side elevational view of the apparatus of FIG. 13 with the top being partially removed.
Figure 15:
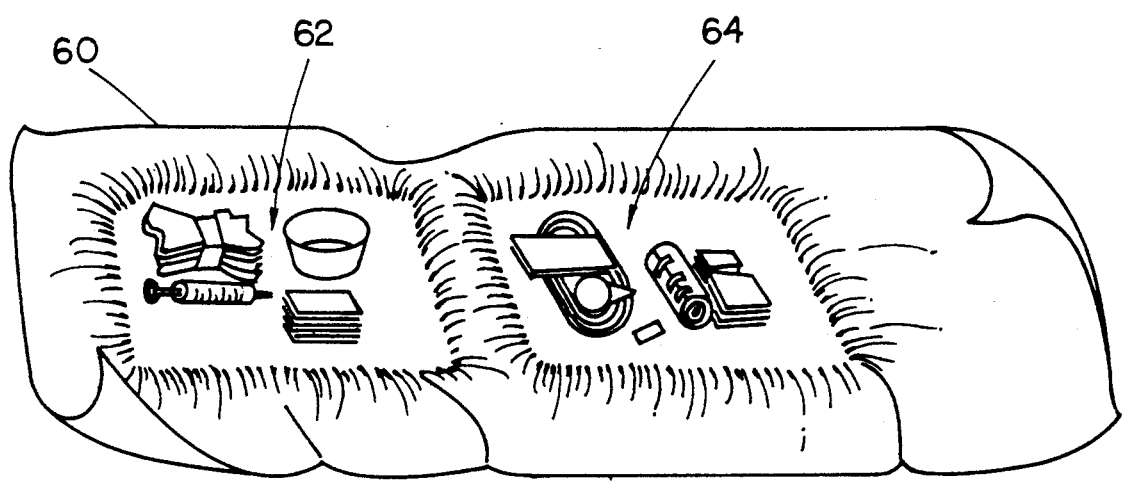
FIG. 15 is a pictorial view of the apparatus of FIG. 13 with the sheet being unfolded.

Referring now more particularly to FIGS. 13 through 15, there is provided yet another embodiment of the invention. The apparatus shown in FIG. 13 is essentially a container 52 which includes surgical tray 54 covered by top 56. The tray and top are sealed together by tape 58 providing sterility for the inside of the container. The inside of the container 52 as shown in FIG. 14 includes sheet 60 which when opened forms a surgical drape. Within the fold of sheet 60 shown in FIG. 15 are various surgical devices 62 and 64 which are laid within the recesses of the tray and top which are covered by drape or sheet 60.

FIGS. 16 through 20 show still another embodiment of the invention. Tray 66 receives surgical apparatus (not shown) and a surgical drape 68 which is folded over the surgical apparatus and is also received under the surgical apparatus in a similar fashion as shown in FIG. 15 except that only a single tray is utilized.

Tray 66 is slidably received in container 70. Preferably container 70 is a corrugated cardboard box which, as can be seen in FIG. 19, includes corrugation 72, inner wall 74 and outer wall 76, and is in the form of an ordinary cardboard box which is commercially available.

The cardboard box should be lined preferably at least one the inside 78, with a material which is impervious to microorganisms such as bacteria but will permit sterilizing gas such as ethylene oxide to pass therethrough. The preferred lining material is medical grade paper such as one which is commercially available from the James River Company. It is believed that a medical grade paper which has a porosity as given by the Gurley-Hill S-P-S Test of about 45 Sec. to 3500 Sec. per 100 milliliters air porosity is acceptable.

It is also preferred that the container 70 be lined with medical grade paper on both the inside and the outside to provide a redundancy of protection in the event that the liner becomes nicked or otherwise fails. As can be seen in FIG. 19, the medical grade paper forms outside liner 80 and inside liner 82 which are respectively attached to walls 76 and 74 by means of an adhesive or other bonding means.

Container 70 also includes flaps 84, 86, 88 and 90 which are used to close the open end after the tray 66 is fully received inside the container 70. Once this occurs, the flaps are closed and the open edges are sealed using a known medical tape 92 which is impervious to bacteria.

The package as shown in FIG. 18 may then be put in the presence of ethylene oxide which will penetrate the layers of medical grade paper 80 and 82 as well as the other parts of the walls of the container and will sterilize the medical instruments and materials as well as the drape 68 which are inside the container. After sterilization has occurred, the container may be placed in the presence of a vacuum or partial vacuum which will cause the ethylene oxide which is inside the container to evacuate therefrom, again penetrating the medical grade paper and the other parts of the walls of the container.

Since the container is primarily in the form of a sealed corrugated box which is impervious to microorganisms including bacteria due to the layer or layers of medical grade paper, the container itself may be used as a shipping container thereby greatly reducing the packaging costs, in particularly eliminating the expensive plastic bag which is often used to enclose packaged surgical materials. Optionally, one may also place container 70 into an inexpensive shipping container in order to avoid the possibility of nicks or cuts on the outer medical grade paper 80. However with medical grade paper 82 being also on the inside of the container, a redundancy is provided and it is believed that unless the package is to be subject to some very rough treatment, an outer container (not shown) is not necessary.

As can be seen in FIG. 20, when tray 66 has been removed from container 70, the drape 68 is spread out thereby providing a sterile field 93. The contents (not shown) which will be in the depression 94 which is created by box 70.

The above described invention eliminates the need for a costly and puncturable sterile bag by using the trays or basins themselves as the package cover. The contents in the package are given greater protection since the walls of the trays or basins are stronger than a sterile bag. The chances of damage to a package are greatly reduced. Furthermore the package is much easier to store and to handle and is cheaper to sterilize and takes up less space.

Since the package is resealable when tape is used it may be used as a handy disposal unit.

From the foregoing description of the preferred embodiments of this invention, it will be apparent that many modifications may be made therein without departing from the true spirit and scope of the invention.

I claim:

1. A surgical package assembly comprising: a first container; said first container having inner and outer surfaces; a sheet initially received inside said first container; means for closing and opening said first container; portions of said sheet attached to said first container; said sheet and said inner surfaces of said first container providing a sterile field when said first container is opened and said sheet is unfolded; said sheet includes first and second openings; said first container received in said first opening; a region of said sheet adjacent to said first opening being attached to said first container; said means for opening and closing said first container includes a second container; said second container received in said second opening; each of said containers being substantially identical, each container having a lip around an opening in each container, a portion of said lip of said first container being in contact with a portion of said lip of said second container when said sheet is on the inside of said first container; said sheet being attached to a part of said lip of each of said containers.

2. A surgical package assembly as set forth in claim 1 further including mean for sealing said containers together.

3. A surgical package assembly as set forth in claim 2 wherein said means to seal is tape.

4. A surgical package assembly as set forth in claim 2 wherein when said containers are sealed together a package is formed and the sterility of the inside of said package may be maintained.

5. A surgical package assembly as set forth in claim 4 wherein said package is adapted to house surgical devices.

6. A surgical package assembly as set forth in claim 1 were said containers are basins.

7. A surgical package assembly as set forth in claim 1 wherein each of said lips are about the outer periphery surface of each of said containers.

8. A method of forming a sterile package utilizing first and second containers and a sheet comprising the steps of: forming first and second openings in said sheet; placing said first container in said first opening; placing said second container in said second opening; attaching said sheet to each of said containers in the regions near each of said openings; sealing said openings; placing the remainder of said sheet inside of said containers; placing said first container on the top of said second container thereby forming an enclosure; sealing said enclosure.

9. A method as set forth in claim 8 further including the steps of:

unsealing said containers; opening said enclosure; placing at least a portion of said sheet on the outside of said containers; opening said sheet; said sheet forming a sterile field.

10. A method as set forth in claim 9 further including the steps of:

placing non-sterile materials inside of said containers; re-sealing said containers.

11. A surgical package assembly comprising:

a disposable container; said container having corrugated cardboard walls forming a boxlike structure;

a tray received in said container; said tray receiving surgical apparatus and a foldable sheet;

a lining made of a medical grade paper; said lining being impervious to bacteria but will pass ethylene oxide sterilization gas; said corrugated cardboard walls being entirely lined on the inside of said boxlike structure with said lining; said lining affixed to said corrugated cardboard walls; wherein the entire surface of said container will pass sterilization gas into and out of said container whereby said container a) protects said tray from mechanical damage thereby obviating the need for further protective packaging, b) ensures sterility of said tray prior to the use of said tray, c) and permits sterilization of said tray.

12. An assembly as set forth in claim 11 further including a layer of medical grade paper on substantially the entire outside of said container.

13. An assembly as set forth in claim 11 wherein when said tray is removed from said container, said sheet may be opened with a portion remaining inside of said tray with the surgical apparatus resting thereon, thereby forming a sterile field on the inside and an area surrounding said tray.

14. An assembly as set forth in claim 11 wherein said container is the sole mechanical protection for said tray during the transportation of said surgical package assembly to the user of said surgical package assembly.

* * * * *